US012642495B2

(12) United States Patent
Zhang et al.

(10) Patent No.: US 12,642,495 B2
(45) Date of Patent: Jun. 2, 2026

(54) CT BEAM HARDENING CORRECTION METHOD, CT BEAM HARDENING CORRECTION DEVICE, AND STORAGE MEDIUM

(71) Applicant: Siemens Shanghai Medical Equipment Ltd., Shanghai (CN)

(72) Inventors: Guo Qing Zhang, Shanghai (CN); Yang Wang, Shanghai (CN); Wei Zhou, Shanghai (CN); Wen Hao Chen, Shanghai (CN)

(73) Assignee: Siemens Shanghai Medical Equipment Ltd., Shanghai (CN)

( * ) Notice: Subject to any disclaimer, the term of this patent is extended or adjusted under 35 U.S.C. 154(b) by 298 days.

(21) Appl. No.: 18/569,330

(22) PCT Filed: Sep. 2, 2021

(86) PCT No.: PCT/CN2021/116208
§ 371 (c)(1),
(2) Date: Dec. 12, 2023

(87) PCT Pub. No.: WO2023/272929
PCT Pub. Date: Jan. 5, 2023

(65) Prior Publication Data
US 2024/0268771 A1 Aug. 15, 2024

(30) Foreign Application Priority Data
Jun. 28, 2021 (CN) .......................... 202110718133.2

(51) Int. Cl.
| | |
|---|---|
| *A61B 6/03* | (2006.01) |
| *A61B 6/00* | (2024.01) |
| *A61B 6/58* | (2024.01) |

(52) U.S. Cl.
CPC ............ *A61B 6/032* (2013.01); *A61B 6/5258* (2013.01); *A61B 6/583* (2013.01)

(58) Field of Classification Search
None
See application file for complete search history.

(56) References Cited

U.S. PATENT DOCUMENTS 9,420,986 B2    8/2016   Yamakawa et al.
2012/0093282 A1*   4/2012   Kappler ............... A61B 6/5205
                                      378/18

(Continued)

FOREIGN PATENT DOCUMENTS

| | | |
|---|---|---|
| CN | 108109183 A | 6/2018 |
| CN | 111080740 A | 4/2020 |

(Continued)

OTHER PUBLICATIONS

Chacko, Michael S., et al. "Impact of beam-hardening corrections on proton relative stopping power estimates from single-and dual-energy CT." Journal of Applied Clinical Medical Physics 23.9 (2022): e13711. (Year: 2022).*

(Continued)

*Primary Examiner* — Michelle M Entezari Hausmann
(74) *Attorney, Agent, or Firm* — Banner & Witcoff, Ltd.

(57) ABSTRACT

Disclosed are techniques for performing CT beam hardening correction. The CT beam hardening correction includes scanning a phantom to obtain measured projection data of the phantom and calculating corrected projection data of a measured object according to a calculated beam hardening correction factor, measured projection data of the measured object, a corrected projection data of the measured object, and a relationship among expected projection data of a scanned object.

13 Claims, 5 Drawing Sheets

(a) Projection data of a 20 cm water phantom (b) Projection data of a 30 cm water phantom (c) Reconstructed image of a 20 cm water phantom (d) Reconstructed image of a 30 cm water phantom

(56) References Cited

U.S. PATENT DOCUMENTS

| | | | |
|---|---|---|---|
| 2014/0321608 A1 | 10/2014 | Ueki et al. | |
| 2016/0183904 A1* | 6/2016 | Lou ..................... | A61B 6/5205 |
| | | | 378/207 |
| 2018/0300879 A1* | 10/2018 | Fu ......................... | A61B 6/032 |

FOREIGN PATENT DOCUMENTS

| | | | |
|---|---|---|---|
| JP | 2015112478 A | * | 6/2015 |
| JP | 5918374 B2 | | 5/2016 |

OTHER PUBLICATIONS

"JP2015112478A" [Machine Translation] (Year: 2015).*
Ghammraoui, Bahaa, et al. "Influence of phantom design on evaluation metrics in photon counting spectral head CT: a simulation study." Journal of Medical Imaging 12.4 (2025): 043501-043501. (Year: 2025).*
Mar. 29, 2022 (PCT) International Search Report—App. PCT/CN2021/116208.
Journal of Hebei University (Natural Science Edition), Issue 06; Nov. 25, 2018; Zhang Xiaoke; Yang Kun; Chen Jintao; Xue Linyan; Li Xiaowei; CT Beam Hardening Correction Method Based on Projection Space; pp. 648-655.

* cited by examiner (a) Projection data of a 20 cm water phantom (b) Projection data of a 30 cm water phantom (c) Reconstructed image of a 20 cm water phantom (d) Reconstructed image of a 30 cm water phantom

CT BEAM HARDENING CORRECTION METHOD, CT BEAM HARDENING CORRECTION DEVICE, AND STORAGE MEDIUM

CROSS-REFERENCE TO RELATED APPLICATIONS

The present application is a U.S. National Stage entry of PCT Application no. PCT/CN2021/116208, filed Sep. 2, 2021, which claims priority to and the benefit of China patent application no. CN 202110718133.2, filed on Jun. 28, 2021, the contents of each of which are incorporated herein by reference in their entireties.

TECHNICAL FIELD

The present disclosure relates to the technical field of computerized tomography (CT) devices and, in particular, to a projection-based CT beam hardening correction method, a CT beam hardening correction device, and a storage medium.

BACKGROUND

In general, X-rays are produced in bremsstrahlung effects and contain broad spectral components. Since low energy X-rays have relatively high attenuation coefficients and are easily absorbed, low energy X-rays attenuate more when passing through objects, and X-ray spectra become "harder" after passing through objects. This means that the proportion of high energy X-rays detected by a detector increases, resulting in a smaller projection value. Because of the beam hardening effect, the attenuation coefficient along the X-ray path is not constant, and this will result in inhomogeneity even in a CT image of a uniform object.

To compensate for this effect, a beam filter may be used to reduce low energy X-rays and increase the average energy of the beam. However, the beam filter will reduce the dose and thus require a higher scanning tube power output, and it will increase the average energy of the X-ray beam and affect low contrast detectability. In addition, it still fails to meet the CT image quality requirements in most clinical scenarios.

Conventionally, in a beam hardening correction method for a CT device, a polynomial fitting correction algorithm is generally applied based on a water phantom. Because water is a main component of a human body, and most beam hardening correction algorithms need to determine polynomial factors for each system, most existing methods for determining a polynomial factor need to determine the polynomial factors in an iterative manner or based on image reconstruction. Since the iterative process and/or image reconstruction are usually inefficient, the entire beam hardening correction process is quite time consuming. Due to time costs, it is difficult or almost impossible to perform the entire correction process for each system.

Therefore, it is desirable to use an effective method to obtain these factors.

SUMMARY

In view of this, the present disclosure proposes a CT beam hardening correction method, a CT beam hardening correction device, and a storage medium. One purpose thereof is to calculate a beam hardening factor by using (e.g. only) projection data of a scanned object without having to perform image reconstruction before calculating the beam hardening factor or iteration, thereby improving calculation efficiency, so that such correction method can be applied to each system in a tuning process of a CT device without adding extra time.

According to one aspect of embodiments of the present disclosure, a CT beam hardening correction method is provided, including: scanning a plurality of phantoms of different sizes by using a beam emitted by a ray source of a CT device, to obtain measured projection data of the plurality of phantoms; calculating estimated theoretical projection data of each phantom based on an initial estimated position of the phantom relative to the ray source by using a theoretical projection data calculation model; calculating an actual position of each phantom relative to the ray source based on the measured projection data of the phantom and the estimated theoretical projection data of the phantom; calculating actual theoretical projection data of each phantom by using the theoretical projection data calculation model according to the actual position of the phantom relative to the ray source; obtaining a beam hardening correction calculation model, where the beam hardening correction calculation model represents a relationship among expected projection data of a scanned object, measured projection data of the scanned object, and a beam hardening correction factor; using the actual theoretical projection data of each phantom as the expected projection data of the scanned object, using the measured projection data of each phantom as the measured projection data of the scanned object, and calculating the beam hardening correction factor according to the relationship by using the beam hardening correction calculation model; and using measured projection data of a measured object as the measured projection data of the scanned object and corrected projection data of the measured object as the expected projection data of the scanned object based on the calculated beam hardening correction factor, and calculating the corrected projection data of the measured object according to the relationship.

In this way, the beam hardening factor can be calculated by using only the projection data of the scanned phantom without performing image reconstruction before the beam hardening factor is calculated and a reconstruction process, thereby improving calculation efficiency so that such method can be applied to each system in a tuning process of a CT device without adding extra time.

In an example according to this embodiment, the beam hardening correction calculation model is represented by the following polynomial expression:

$$P_{exp} = P_{mea} \cdot \sum\nolimits_{i,j=0}^{3} f_{i,j} \cdot (P_{mea} + B)^i \cdot B^j,$$

where $i+j \leq 3$; where $P_{exp}$ represents the expected projection data of the scanned object, $P_{mea}$ represents the measured projection data of the scanned object, B represents an inherent attenuation value of a wedge filter, and $f_{i,j}$ represents the beam hardening correction factor.

In this manner, the polynomial expression of the beam hardening correction model is preset, and then the beam hardening correction factor is obtained according to the actual theoretical projection data of the phantom and the measured projection data of the phantom. Compared with a conventional method in which a polynomial factor is obtained by using an image obtained by scanning a homogeneous phantom and the polynomial factor is solved in an iterative manner, the method in this application can avoid image reconstruction and iterative processes, and can be applied to each system in a tuning process of a CT device without adding extra time.

In an example of this embodiment, the calculating the beam hardening correction factor according to the relationship includes: substituting the actual theoretical projection data $P^{sim}$ of each phantom as the expected projection data of the scanned object, and the measured projection data P of each phantom as the measured projection data of the scanned object into the polynomial expression of the beam hardening correction calculation model to obtain the following expression (1):

$$P^{sim} = P \cdot \sum\nolimits_{i,j=0}^{3} f_{i,j} \cdot (P+B)^i \cdot B^j,$$

where i+j≤3; where if $V_{i,j} = P \cdot (P+B)^i \cdot B^j$, expression (1) is expressed as the following matrix calculation formula:

$$\begin{bmatrix} V_{0,0,1} & \cdots & V_{0,3,1} \\ \vdots & V_{i,j,k} & \vdots \\ V_{0,0,N} & \cdots & V_{0,3,N} \end{bmatrix} \begin{bmatrix} f_{0,0} \\ \vdots \\ f_{i,j} \\ \vdots \\ f_{0,3} \end{bmatrix} = \begin{bmatrix} P_1^{sim} \\ \vdots \\ P_k^{sim} \\ \vdots \\ P_N^{sim} \end{bmatrix};$$

and solving the matrix calculation formula by using the least square method to calculate the beam hardening correction factor $f_{i,j}$, where k is a detector pixel index and N is the total amount of pixel data.

In this manner, calculation complexity of the beam hardening correction factor $f_{i,j}$ can be simplified and accuracy of determining the beam hardening correction factor $f_{i,j}$ can be improved.

In an example of this embodiment, the calculating corrected projection data of the measured object according to the relationship includes: substituting the measured projection data $P_1$ of the measured object as the measured projection data of the scanned object and the corrected projection data $P_{BHC}$ of the measured object as the expected projection data of the scanned object into the polynomial expression of the beam hardening correction calculation model to obtain the following expression (2):

$$P_{BHC} = P_1 \cdot \sum\nolimits_{i,j=0}^{3} f_{i,j} \cdot (P_1+B)^i \cdot B^j,$$

where i+j≤3; and calculating the corrected projection data $P_{BHC}$ of the measured object based on the calculated beam hardening correction factor $f_{i,j}$ and the measured projection data $P_1$ of the measured object by using expression (2).

In this manner, attenuation of a unit distance between a high-energy ray and a low-energy ray in a beam emitted by the ray source along an X-ray path is basically the same, so that an image reconstructed from projection data detected by a detector (array) has little beam hardening artifact.

In an example according to this embodiment, the ray source is a scanning tube, and the total amount N of the pixel data is equal to the quantity of the phantoms×the quantity of positions of the phantoms×the quantity of scanning positions of the scanning tube×the quantity of the detector pixels.

In this manner, the beam hardening correction method in this application can be made more robust, and can be adapted to measured objects of different sizes, for example, adults and children of different heights.

In an example according to this embodiment, the scanning tube performs scanning at a predetermined angle interval. For example, the predetermined angle interval may π/6.

In this manner, calculation time can be reduced.

In an example according to this embodiment, the measured projection data of the plurality of phantoms includes measured projection data obtained by scanning each phantom at a plurality of phantom positions of the phantom and a plurality of scanning spherical tube positions.

In this manner, the beam hardening correction method in this application can be more robust.

In an example of this embodiment, the theoretical projection data calculation model is represented as $P_t = \mu l = \mu_1 l_1 + \mu_2 l_2$, where $P_t$ represents the theoretical projection data of the phantom, $\mu_1$ and $\mu_2$ are respectively attenuation coefficients of a housing of the phantom and a uniform filler in the housing, $l_1$ is a path length of a ray that is in the beam and that is angled at β relative to a center line of the beam in the housing, $l_2$ is a path length of the ray in the filler, and $l_1$ and $l_2$ are calculated by using the following formulas:

$$l_1 = 2 \cdot \sqrt{r_1^2 - d^2} - l_2;$$
$$l_2 = 2 \cdot \sqrt{r_2^2 - d^2}; \text{ and}$$
$$d = D \cdot \sin(\beta - \beta_0),$$

where D represents a distance between the ray source of the beam and the center of the phantom, $\beta_0$ represents an angle between a line connecting the ray source of the beam and the center of the phantom and a center line of the beam, β represents an angle between the ray and the center line of the beam, $r_1$ represents a radius of the housing of the phantom, $r_2$ represents a radius of the filler of the phantom, and d represents a vertical distance between the center of the phantom and the ray.

In this manner, the theoretical projection data of the phantom can be determined by using a simple calculation process.

In an example according to this embodiment, the initial estimated position of each phantom relative to the ray source of the beam includes an initial estimated distance D' between the ray source of the beam and the center of the phantom and an initial estimated angle $\beta_0$' between the line connecting the ray source of the beam and the center of the phantom and the center line of the beam, and the calculating estimated theoretical projection data of each phantom based on an initial estimated position of the phantom relative to the ray source of the beam by using a theoretical projection data calculation model includes: presetting the initial estimated distance D' and the initial estimated angle $\beta_0$'; and substituting the initial estimated distance D' as the distance D between the ray source of the beam and the center of the phantom and the initial estimated angle $\beta_0$' as the angle $\beta_0$ between the line connecting the ray source of the beam and the center of the phantom and the center line of the beam into the theoretical projection data calculation model to calculate the estimated theoretical projection data.

In this manner, the initial estimated position of each phantom relative to the ray source of the beam is estimated according to experience, and the theoretical projection data is estimated according to the initial estimated position, thereby simplifying a calculation process.

In an example according to this embodiment, the actual position of each phantom relative to the ray source of the beam includes an actual distance D" between the ray source of the beam and the center of the phantom and an actual angle $\beta_0$" between the line connecting the ray source of the beam and the center of the phantom and the center line of the beam, and the calculating an actual position of each phantom relative to the ray source of the beam based on the measured projection data of the phantom and the estimated theoretical projection data of the phantom includes: determining the actual distance D" and the actual angle $\beta_0$" by minimizing the sum of the differences of squares of the measured projection data and the calculated estimated theoretical projection data by using a simplex multi-parameter optimization method.

In this manner, the initial estimated position of each phantom relative to the ray source of the beam can be corrected based on the measured projection data of the phantom, and therefore, the actual position of each phantom relative to the ray source of the beam can be accurately determined.

In an example of this embodiment, the calculating actual theoretical projection data of each phantom by using the theoretical projection data calculation model according to the actual position of the phantom relative to the ray source of the beam includes: substituting the determined actual distance D" as the distance D between the ray source of the beam and the center of the phantom and the actual angle $\beta_0$" as the angle $\beta_0$ between the line connecting the ray source of the beam and the center of the phantom and the center line of the beam into the theoretical projection data calculation model to calculate the actual theoretical projection data of each phantom.

In this manner, the actual theoretical projection data of the phantom can be accurately determined by reducing calculation complexity.

According to another aspect of the embodiments of the present disclosure, a CT beam hardening correction device is provided, including: an estimated theoretical projection data calculation module, configured to calculate estimated theoretical projection data of each phantom based on an initial estimated position of the phantom relative to the ray source by using a theoretical projection data calculation model; a phantom actual position calculation module, configured to calculate an actual position of each phantom relative to the ray source of the beam based on measured projection data of each phantom obtained by scanning a plurality of phantoms of different sizes by using a beam emitted by a CT device and the estimated theoretical projection data of each phantom; an actual theoretical projection data calculation module, configured to calculate actual theoretical projection data of each phantom by using the theoretical projection data calculation model according to the actual position of the phantom relative to the ray source of the beam; a beam hardening correction calculation model obtaining module, configured to obtain a beam hardening correction calculation model, where the beam hardening correction calculation model represents a relationship among expected projection data of a scanned object, measured projection data of the scanned object, and a beam hardening correction factor; a beam hardening correction factor calculation module, configured to use the actual theoretical projection data of each phantom as the expected projection data of the scanned object, use the measured projection data of each phantom as the measured projection data of the scanned object, and calculate the beam hardening correction factor according to the relationship by using the beam hardening correction calculation model; and a measured projection data correction module for a measured object, configured to: use measured projection data of a measured object as the measured projection data of the scanned object and corrected projection data of the measured object as the expected projection data of the scanned object based on the calculated beam hardening correction factor, and calculate the corrected projection data of the measured object according to the relationship.

In this manner, the beam hardening factor can be calculated by using only the projection data of the scanned object without performing image reconstruction before the beam hardening factor is calculated, and no iterative process is required in the calculation process. Therefore, calculation efficiency can be improved, so that such correction method can be applied to each system in a tuning process of a CT device without adding extra time.

According to still another aspect of the embodiments of the present disclosure, a storage medium storing a program is provided. When a processor executes the program, the program causes the processor to perform the foregoing CT beam hardening correction method.

It can be learned from the foregoing solutions that, in the present disclosure, the beam hardening factor can be calculated by using only the projection data of the scanned object without performing image reconstruction before the beam hardening factor is calculated, and no iterative process is required in the calculation process. Therefore, calculation efficiency can be improved, so that such correction method can be applied to each system in a tuning process of a CT device without adding extra time.

BRIEF DESCRIPTION OF THE DRAWINGS

To enable a person of ordinary skill in the art to understand the foregoing and other features and advantages of the present disclosure more clearly, exemplary embodiments of the present disclosure are described in detail below with reference to the accompany drawings. In the accompany drawings.

Figure 1:
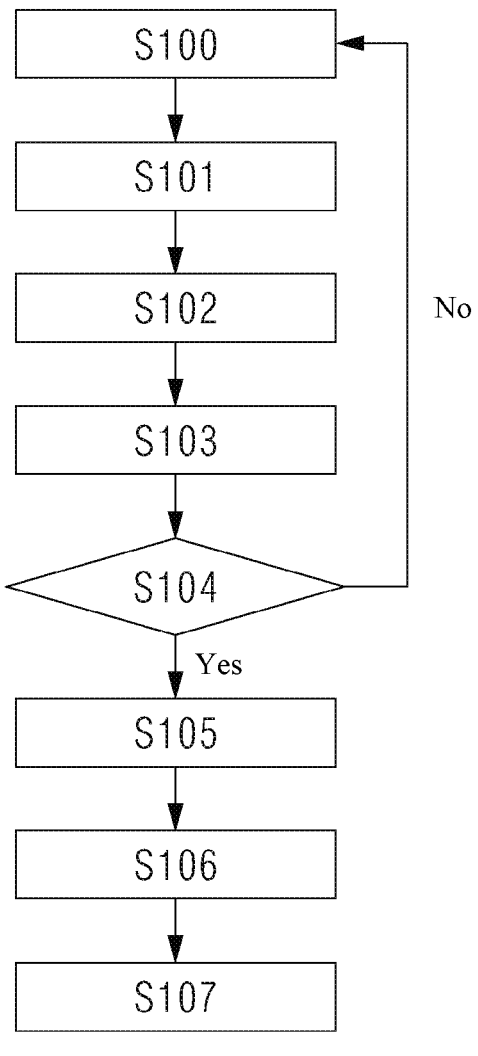
FIG. 1 illustrates a flowchart of a CT beam hardening correction method according to an embodiment of this disclosure.

Reference numerals are as follows:

500 CT beam hardening correction device

501 Estimated theoretical projection data calculation module

502 Phantom actual position calculation module

503 Actual theoretical projection data calculation module

504 Beam hardening correction calculation model obtaining module

505 Beam hardening correction factor calculation module

506 Measured projection data correction module

S100-S107 Blocks

DETAILED DESCRIPTION OF THE DISCLOSURE

To make the objectives, technical solutions, and advantages of the present disclosure clearer, the following further describes the present disclosure with reference to the embodiments.

FIG. 1 illustrates a flowchart of a CT beam hardening correction method according to an embodiment of this disclosure. As shown in FIG. 1, the CT beam hardening correction method according to this embodiment of the present disclosure includes the following blocks:

Block S100: Scan a plurality of phantoms of different sizes by using a beam emitted by a ray source of a CT device, to obtain measured projection data of the plurality of phantoms.

Figure 2A:
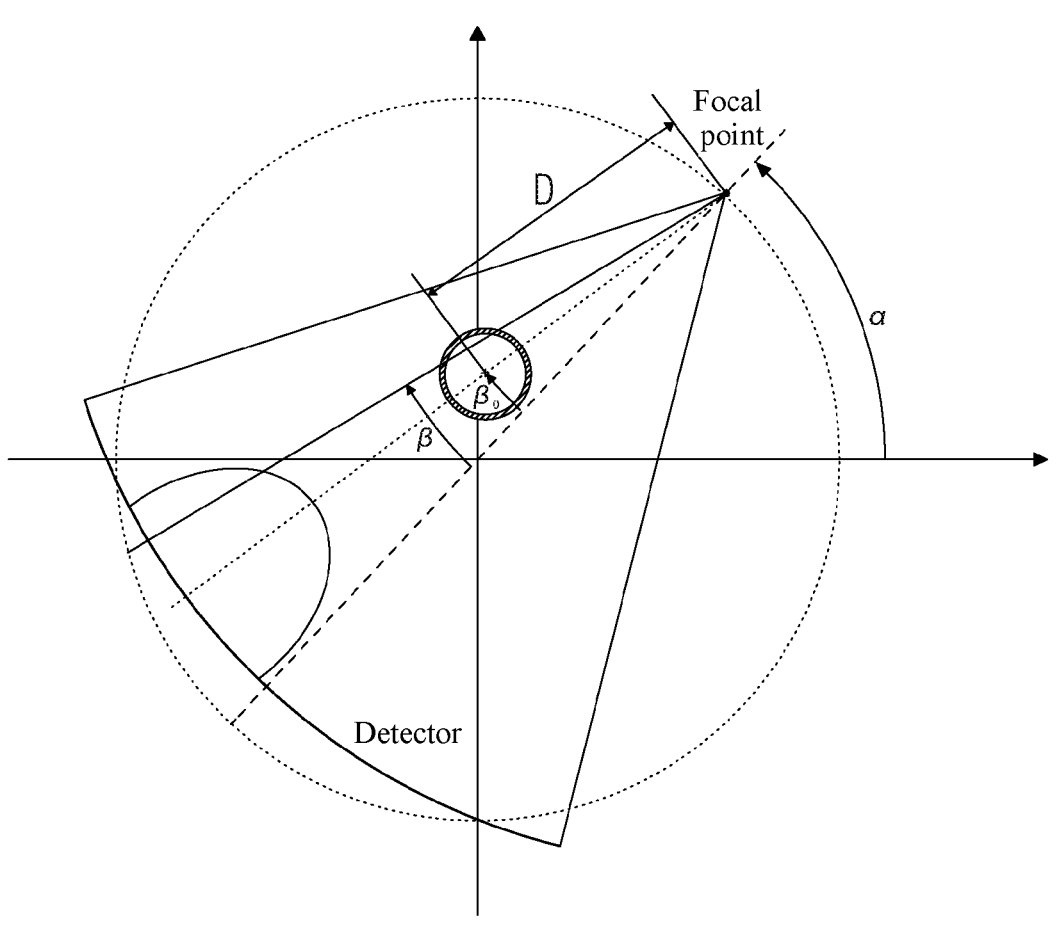
FIG. 2A illustrates a schematic diagram of a positional relationship between a ray source, a phantom, a detector, and a beam.

The ray source may include a scanning tube, and the scanning tube may scan the phantom at a predetermined angle interval a (as shown in FIG. 2A), for example, an angle interval $\pi/6$; and may scan each phantom relative to the ray source at different positions of the CT device. For example, the phantom may be scanned in a rotation center, and the phantom may be eccentrically scanned. Therefore, the measured projection data of the plurality of phantoms includes measured projection data obtained by scanning each phantom at a plurality of phantom positions of the phantom and a plurality of scanning tube positions.

Block S101: Calculate estimated theoretical projection data of each phantom based on an initial estimated position of the phantom relative to the ray source by using a theoretical projection data calculation model (in FIG. 2A, the ray source is an X-ray scanning tube, and the scanning tube is represented by a focal point thereof).

The theoretical projection data calculation model is expressed as the following formula:

$$P_t = \mu l = \mu_1 l_1 + \mu_2 l_2,$$

Figure 2B:
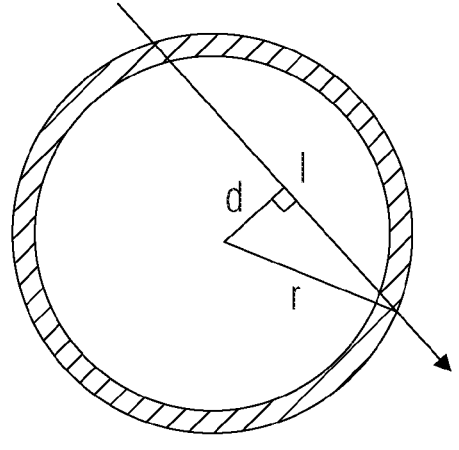
FIG. 2B illustrates a schematic diagram of a positional relationship between a phantom and a ray in a beam.

$P_t$ represents the theoretical projection data of the phantom, $\mu_1$ and $\mu_2$ are respectively attenuation coefficients of a housing of the phantom and a uniform filler in the housing, $l_1$ is a path length of a ray that is in the beam and that is angled at $\beta$ relative to a center line of the beam in the housing, $l_2$ is a path length of the ray in the filler, and $l_1$ and $l_2$ are calculated by using the following formulas according to the positional relationship among the phantom, the ray source, and the beam shown in FIG. 2A and FIG. 2B:

$$l_1 = 2 \cdot \sqrt{r_1^2 - d^2} - l_2;$$

$$l_2 = 2 \cdot \sqrt{r_2^2 - d^2}; \text{ and}$$

$$d = D \cdot \sin(\beta - \beta_0),$$

where

D is the distance between the ray source of the beam and the center of the phantom, $\beta_0$ represents the angle between the line connecting the ray source of the beam and the center of the phantom and the center line of the beam, $\beta$ represents the angle between the ray and the center line of the beam, $r_1$ represents the radius of the housing of the phantom, $r_2$ represents the radius of the filler of the phantom, and d is the vertical distance between the center of the phantom and the ray. Herein, the phantom may be a water phantom for simulating a human body. The housing of the phantom is made of PMMA materials, and the filler in the housing is water.

In this specification, the term "projection data" is used to indicate the attenuation amount.

The initial estimated position of each phantom relative to the ray source of the beam includes an initial estimated distance D' between the ray source of the beam and the center of the phantom and an initial estimated angle $\beta_0'$ between the line connecting the ray source of the beam and the center of the phantom and the center line of the beam, and the initial estimated distance D' and the initial estimated angle $\beta_0'$ may be initially set. Then, the initial estimated distance D' as the distance D between the ray source of the beam and the center of the phantom and the initial estimated angle $\beta_0'$ as the angle $\beta_0$ between the line connecting the ray source of the beam and the center of the phantom and the center line of the beam are substituted into formula $d=D \cdot \sin(\beta-\beta_0)$, so as to obtain the vertical distance d between the center of the phantom and the ray. Then the calculated vertical distance d is substituted into formula $$l_2 = 2 \cdot \sqrt{r_2^2 - d^2}$$

to obtain the path length $l_2$ of the ray in the filler. The obtained path length $l_2$ of the ray in the filler and the obtained vertical distance d are substituted into formula $$l_1 = 2 \cdot \sqrt{r_1^2 - d^2} - l_2$$

to obtain that $l_1$ is the path length $l_1$ that is of the ray in the beam in the housing and that is angled at $\beta$ relative to the center line of the beam. Then, the estimated theoretical projection data is calculated according to expression $P_t=\mu l=\mu_1 l_1+\mu_2 l_2$ of the theoretical projection data calculation model.

Block S102: Calculate an actual position of each phantom relative to the ray source the beam based on the measured projection data of the phantom and the estimated theoretical projection data of the phantom.

Figure 3:
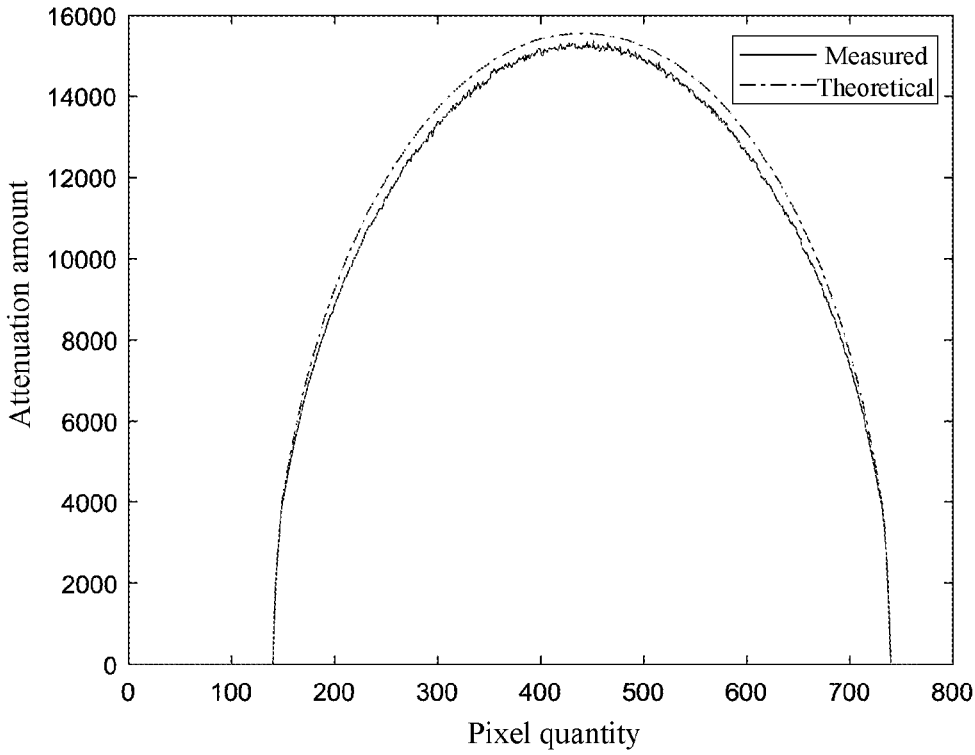
FIG. 3 illustrates is a graph of measured projection data of a phantom and estimated theoretical projection data of the phantom.
Figure 4:
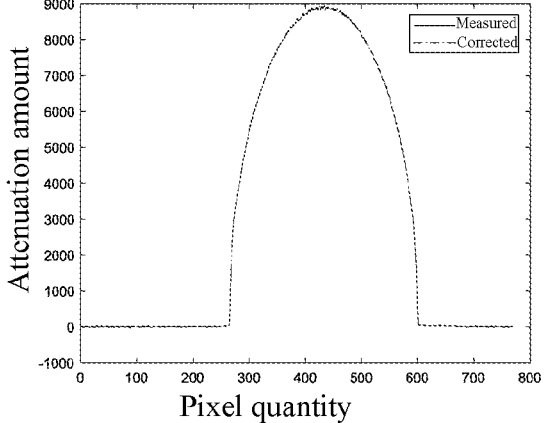
FIG. 4 illustrates measured projection data of a 20 cm water phantom and a 30 cm water phantom of a measured object, a graph of corrected projection data obtained after the measured projection data of the 20 cm water phantom and the 30 cm water phantom of the measured object are corrected by using the CT beam hardening correction method provided in the embodiment of the present disclosure, and a diagram of a constructed image.
Figure 4:
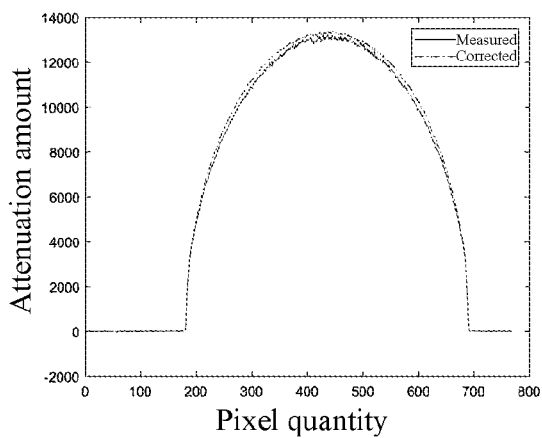
Figure 4:
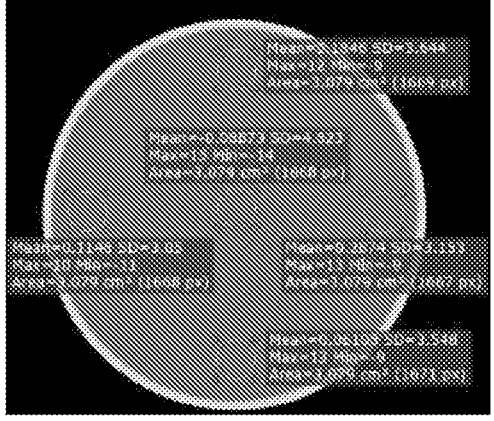
Figure 4:
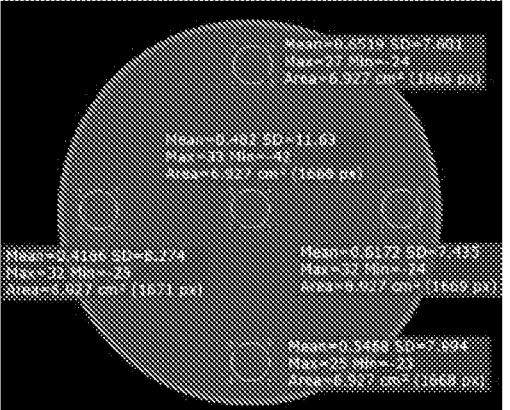

Specifically, the actual position of each phantom relative to the ray source of the beam includes an actual distance D" between the ray source of the beam and the center of the phantom and an actual angle $\beta_0''$ between the line connecting the ray source of the beam and the center of the phantom and the center line of the beam, and the actual distance D" and the actual angle $\beta_0''$ are determined by minimizing the sum of the differences of squares of the measured projection data (measured attenuation amount) of the phantom shown in FIG. 3 and the calculated estimated theoretical projection data (estimated theoretical attenuation amount) by using a simplex multi-parameter optimization method.

Block S103: Calculate actual theoretical projection data of each phantom by using the theoretical projection data calculation model according to the actual position of the phantom relative to the ray source of the beam.

Specifically, the determined actual distance D" as the distance D between the ray source of the beam and the center of the phantom and the actual angle $\beta_0$" as the angle $\beta_0$ between the line connecting the ray source of the beam and the center of the phantom and the center line of the beam are substituted into the theoretical projection data calculation model to calculate the actual theoretical projection data of each phantom.

The foregoing blocks S100-S103 are repeated for each phantom of the plurality of phantoms and a plurality of positions of each phantom (that is, a plurality of positions of the phantom relative to the tube), and it is determined at block S104 whether the foregoing blocks S100-S103 have been performed for all the phantoms and all the positions of the phantoms. If yes, block S105 is performed. If no, block S100 is performed.

Block S105: Obtain a beam hardening correction calculation model, where the beam hardening correction calculation model represents a relationship among expected projection data of a scanned object, measured projection data of the scanned object, and a beam hardening correction factor.

The beam hardening correction calculation model is represented by the following polynomial expression:

$$P_{exp} = P_{mea} \cdot \sum\nolimits_{i,j=0}^{3} f_{i,j} \cdot (P_{mea} + B)^i \cdot B^j, \text{ where } i + j \le 3;$$

where $P_{exp}$ represents the expected projection data of the scanned object, $P_{mea}$ represents the measured projection data of the scanned object, B represents an inherent attenuation value of a wedge filter, and $f_{i,j}$ represents the beam hardening correction factor.

Block S106: Use the actual theoretical projection data of each phantom as the expected projection data of the scanned object, use the measured projection data of each phantom as the measured projection data of the scanned object, and calculate the beam hardening correction factor according to the relationship by using the beam hardening correction calculation model.

Specifically, the actual theoretical projection data $P^{sim}$ of each phantom as the expected projection data of the scanned object, and the measured projection data P of each phantom as the measured projection data of the scanned object and are substituted into the polynomial expression of the beam hardening correction calculation model to obtain the following expression (1):

$$P^{sim} = P \cdot \sum\nolimits_{i,j=0}^{3} f_{i,j} \cdot (P + B)^i \cdot B^j, \text{ where } i + j \le 3;$$

where if $V_{i,j} = P \cdot (P+B)^i \cdot B^j$, expression (1) is expressed as the following matrix calculation formula:

$$\begin{bmatrix} V_{0,0,1} & \cdots & V_{0,3,1} \\ \vdots & V_{i,j,k} & \vdots \\ V_{0,0,N} & \cdots & V_{0,3,N} \end{bmatrix} \begin{bmatrix} f_{0,0} \\ \vdots \\ f_{i,j} \\ \vdots \\ f_{0,3} \end{bmatrix} = \begin{bmatrix} P_1^{sim} \\ \vdots \\ P_k^{sim} \\ \vdots \\ P_N^{sim} \end{bmatrix}.$$

Then, the matrix calculation formula is solved by using the least square method to calculate the beam hardening correction factor $f_{i,j}$, where k represents a detector pixel index and N is the total amount of pixel data.

For example, the ray source may be a scanning tube, and the total amount N of the pixel data is equal to the quantity of the phantoms×the quantity of positions of the phantoms× the quantity of scanning positions of the scanning tube×the quantity of the detector pixels.

The scanning tube may perform, for example, scanning at a predetermined angle interval such as $\pi/6$, so that calculation time can be reduced.

Block S107: Use measured projection data of a measured object as the measured projection data of the scanned object and corrected projection data of the measured object as the expected projection data of the scanned object based on the calculated beam hardening correction factor, and calculate the corrected projection data of the measured object according to the relationship.

Specifically, the measured projection data $P_1$ of the measured object as the measured projection data of the scanned object and the corrected projection data $P_{BHC}$ of the measured object as the expected projection data of the scanned object are substituted into the polynomial expression of the beam hardening correction calculation model to obtain the following expression (2):

$$P_{BHC} = P_1 \cdot \sum\nolimits_{i,j=0}^{3} f_{i,j} (P_1 + B)^i \cdot B^j, \text{ where } i + j \le 3.$$

Then, the corrected projection data $P_{BHC}$ of the measured object is calculated based on the calculated beam hardening correction factor $f_{i,j}$ and the measured projection data $P_1$ of the measured object by using expression (2).

The foregoing CT beam hardening correction method in this application may be applied to rotation scanning and static scanning, and the foregoing CT beam hardening correction method is further applicable to various phantoms that are equivalent to human tissues and have a known attenuation coefficient.

Figure 5:
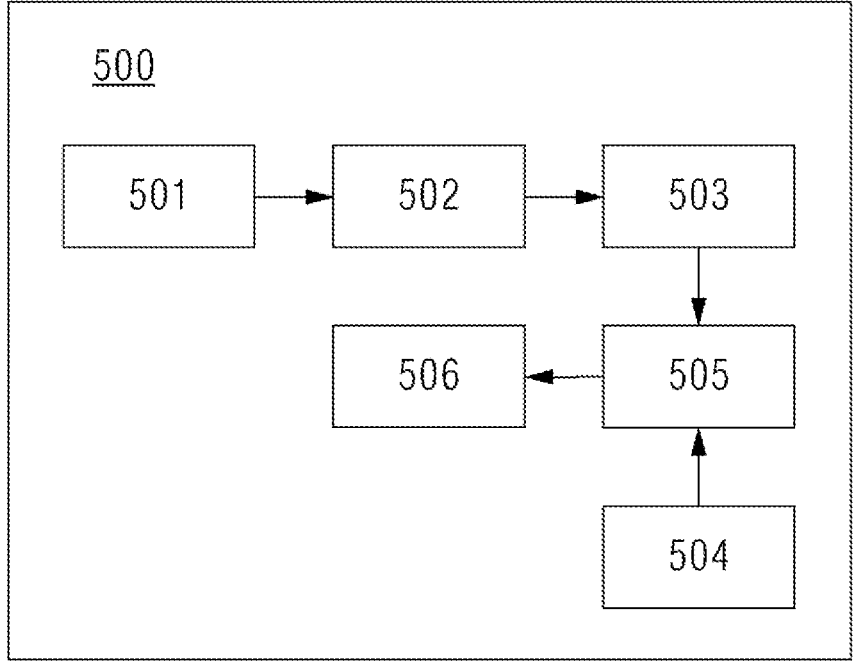
FIG. 5 illustrates a block diagram of a CT beam hardening correction device according to an embodiment of the present disclosure.

FIG. 5 shows measured projection data of a 20 cm water phantom and a 30 cm water phantom of a measured object, a graph of corrected projection data obtained after the measured projection data of the 20 cm water phantom and the 30 cm water phantom of the measured object are corrected by using the CT beam hardening correction method provided in the embodiment of the present disclosure, and an instance of a constructed image. As can be seen from the constructed image, the maximum average difference between the peripheral region of interest (ROI) and the central ROI of the 20 cm water phantom is less than 1 Hounsfield unit (HU, used for CT image measurement, which may also be referred to as a CT value), and the maximum average difference between the peripheral ROI and the central ROI of the 30 cm water phantom is about 1 HU, which can clearly meet a uniformity requirement of a CT factory delivery system.

FIG. 5 shows a CT beam hardening correction device 500 corresponding to the CT beam hardening correction method in FIG. 1. The CT beam hardening correction device 500 performs steps of the CT beam hardening correction method in FIG. 1. The CT beam hardening correction device 500 may include: an estimated theoretical projection data calculation module 501, configured to receive an initially set initial estimated position of each phantom relative to a ray source of a beam, and calculate estimated theoretical projection data of each phantom based on the initial estimated position of the phantom relative to the ray source by using a theoretical projection data calculation model; a phantom actual position calculation module 502, configured to receive from a detector (array) measured projection data of each phantom obtained by scanning a plurality of phantoms of different sizes by using a beam emitted by a ray source of a CT device, receive the estimated theoretical projection data of each phantom from the estimated theoretical projection data calculation module 501, and calculate an actual position of each phantom relative to the ray source of the beam based on the measured projection data of each phantom and the estimated theoretical projection data of each phantom; an actual theoretical projection data calculation module 503, configured to receive the actual position of each phantom relative to the ray source of the beam from the phantom actual position calculation module 502, and calculate actual theoretical projection data of each phantom by using the theoretical projection data calculation model according to the actual position of the phantom relative to the ray source of the beam; a beam hardening correction calculation model obtaining module 504, configured to obtain a beam hardening correction calculation model from an external or internal memory, where the beam hardening correction calculation model represents a relationship among expected projection data of a scanned object, measured projection data of the scanned object, and a beam hardening correction factor; a beam hardening correction factor calculation module 505, configured to receive the beam hardening correction calculation model from the beam hardening correction calculation model obtaining module 504, use the actual theoretical projection data of each phantom as the expected projection data of the scanned object, use the measured projection data of each phantom as the measured projection data of the scanned object, and calculate the beam hardening correction factor according to the relationship by using the beam hardening correction calculation model; and a measured projection data correction module for a measured object 506, configured to: use measured projection data of a measured object as the measured projection data of the scanned object and corrected projection data of the measured object as the expected projection data of the scanned object based on the calculated beam hardening correction factor, and calculate the corrected projection data of the measured object according to the relationship.

Further, the beam hardening correction method in this application may be stored in a computer storage medium as a program, and a processor may read the program from the computer storage medium and execute the program, so as to perform the beam hardening correction method.

The foregoing descriptions are merely preferred embodiments of the present disclosure, but are not intended to limit the present disclosure. Any modification, equivalent replacement, or improvement made within the spirit and principle of the present disclosure shall fall within the protection scope of the present disclosure.

What is claimed is:

1. A computerized tomography (CT) beam hardening correction method, comprising:

scanning a plurality of phantoms of different sizes using a beam emitted via a ray source of a CT device to obtain measured projection data of the plurality of phantoms;

calculating estimated theoretical projection data of each one of the plurality of phantoms based on an initial estimated position of each respective phantom relative to the ray source using a theoretical projection data calculation model;

calculating an actual position of each one of the plurality of phantoms relative to the ray source based on the measured projection data of the phantom and the estimated theoretical projection data of each respective phantom;

calculating actual theoretical projection data of each one of the plurality of phantoms using the theoretical projection data calculation model according to the actual position of each respective phantom relative to the ray source;

obtaining a beam hardening correction calculation model, wherein the beam hardening correction calculation model represents a relationship among expected projection data of a scanned object, measured projection data of the scanned object, and a beam hardening correction factor;

using the actual theoretical projection data of each one of the plurality of phantoms as the expected projection data of the scanned object;

using the measured projection data of each one of the plurality of phantoms as the measured projection data of the scanned object;

calculating the beam hardening correction factor according to the relationship using the beam hardening correction calculation model; and using measured projection data of a measured object as the measured projection data of the scanned object and corrected projection data of the measured object as the expected projection data of the scanned object based on the calculated beam hardening correction factor; and calculating the corrected projection data of the measured object according to the relationship.

2. The CT beam hardening correction method according to claim 1, wherein the beam hardening correction calculation model is represented in accordance with a polynomial expression:

$$P_{exp} = P_{mea} \cdot \sum\nolimits_{i,j=0}^{3} f_{i,j} \cdot (P_{mea} + B)^i \cdot B^j,$$

wherein $$i + j \le 3,$$

$P_{exp}$ represents the expected projection data of the scanned object, $P_{mea}$ represents the measured projection data of the scanned object, B represents an inherent attenuation value of a wedge filter, and $f_{i,j}$ represents the beam hardening correction factor.

3. The CT beam hardening correction method according to claim 2, wherein calculating the beam hardening correction factor according to the relationship comprises:

substituting the actual theoretical projection data $P^{sim}$ of each one of the plurality of phantoms as the expected projection data of the scanned object, and substituting the measured projection data P of each one of the plurality of phantoms as the measured projection data of the scanned object into the polynomial expression of the beam hardening correction calculation model to obtain the following expression (1):

$$P^{sim} = P \cdot \sum_{i,j=0}^{3} f_{i,j} \cdot (P+B)^i \cdot B^j,$$

wherein $$i + j \leq 3$$

if $f_{i,j} = V_{i,j} = P \cdot (P+B)^i \cdot B^j$, expression (1) is expressed as the following matrix formula:

$$\begin{bmatrix} V_{0,0,1} & \cdots & V_{0,3,1} \\ \vdots & V_{i,j,k} & \vdots \\ V_{0,0,N} & \cdots & V_{0,3,N} \end{bmatrix} \begin{bmatrix} f_{0,0} \\ \vdots \\ f_{i,j} \\ \vdots \\ f_{0,3} \end{bmatrix} = \begin{bmatrix} P_1^{sim} \\ \vdots \\ P_k^{sim} \\ \vdots \\ P_N^{sim} \end{bmatrix}; \text{ and}$$

solving the matrix formula by using a least squares method to calculate the beam hardening correction factor $f_{i,j}$, wherein k represents a detector pixel index and N represents a total amount of pixel data.

4. The CT beam hardening correction method according to claim 3, wherein calculating the corrected projection data of the measured object according to the relationship comprises:

substituting a measured projection data $P_1$ of the measured object as the measured projection data of the scanned object and substituting a corrected projection data $P_{BHC}$ of the measured object as the expected projection data of the scanned object into the polynomial expression of the beam hardening correction calculation model to obtain the following expression (2):

$$P_{BHC} = P_1 \cdot \sum_{i,j=0}^{3} f_{i,j} \cdot (P_1 + B)^i \cdot B^j,$$

calculating the corrected projection data $P_{BHC}$ of the measured object based on the calculated beam hardening correction factor $f_{i,j}$ and the measured projection data $P_1$ of the measured object using expression (2).

5. The CT beam hardening correction method according to claim 4, wherein the calculating actual theoretical projection data of each one of the plurality of phantoms using the theoretical projection data calculation model according to the actual position of the phantom relative to the ray source of the beam comprises:

substituting the determined actual distance D" as the distance D between the ray source of the beam and the center of the phantom and substituting the actual angle $\beta_0$" as the angle $\beta_0$ between the line connecting the ray source of the beam and the center of the phantom and the center line of the beam into the theoretical projection data calculation model to calculate the actual theoretical projection data of each phantom.

6. The CT beam hardening correction method according to claim 3, wherein the ray source comprises a scanning tube, and wherein the total amount N of the pixel data is equal to the number of the of the plurality of phantoms×a quantity of positions of the plurality of phantoms×a quantity of scanning positions of the scanning tube×a quantity of detector pixels.

7. The CT beam hardening correction method according to claim 6, wherein the scanning tube performs the scanning at a predetermined angle interval.

8. The CT beam hardening correction method according to claim 7, wherein the measured projection data of the plurality of phantoms comprises measured projection data obtained by scanning each one of the plurality of phantoms at a plurality of phantom positions of each phantom and a plurality of scanning tube positions.

9. The CT beam hardening correction method according to claim 1, wherein:

the theoretical projection data calculation model is represented as:

$$P_t = \mu l = \mu_1 l_1 + \mu_2 l_2,$$

wherein $P_t$ represents theoretical projection data of the phantom, $\mu_1$ and $\mu_2$ respectively represent attenuation coefficients of a housing of the phantom and a uniform filler in the housing, $l_1$ represents a path length of a ray that is in the beam and that is angled at $\beta$ relative to a center line of the beam in the housing, $l_2$ represents a path length of the ray in the filler, and $l_1$ and $l_2$ are calculated by using the following formulas:

$$l_1 = 2 \cdot \sqrt{r_1^2 - d^2} - l_2;$$

$$l_2 = 2 \cdot \sqrt{r_2^2 - d^2}; \text{ and}$$

$$d = D \cdot \sin(\beta - \beta_0),$$

wherein:

D represents a distance between the ray source of the beam and the center of the phantom, $\beta_0$ represents an angle between a line connecting the ray source of the beam and the center of the phantom and a center line of the beam, $\beta$ represents an angle between the ray and the center line of the beam, $r_1$ represents a radius of the housing of the phantom, $r_2$ represents a radius of the filler of the phantom, and d represents a vertical distance between the center of the phantom and the ray.

10. The CT beam hardening correction method according to claim 9, wherein the initial estimated position of each one of the plurality of phantoms relative to the ray source of the beam comprises an initial estimated distance D' between the ray source of the beam and the center of the phantom, and an initial estimated angle $\beta_0$' between the line connecting the ray source of the beam and the center of the phantom and the center line of the beam, and the calculating estimated theoretical projection data of each phantom based on an initial estimated position of the phantom relative to the ray source of the beam by using a theoretical projection data calculation model comprises:

presetting the initial estimated distance D' and the initial estimated angle $\beta_0$'; and substituting the initial estimated distance D' as the distance D between the ray source of the beam and the center of the phantom and substituting the initial estimated angle $\beta_0'$ as the angle $\beta_0$ between the line connecting the ray source of the beam and the center of the phantom, and substituting the center line of the beam into the theoretical projection data calculation model to calculate the estimated theoretical projection data.

11. The CT beam hardening correction method according to claim 10, wherein:

the actual position of each phantom relative to the ray source of the beam comprises an actual distance D" between the ray source of the beam and the center of the phantom and an actual angle $\beta_0$" between the line connecting the ray source of the beam and the center of the phantom and the center line of the beam, and calculating an actual position of each phantom relative to the ray source of the beam based on the measured projection data of the phantom and the estimated theoretical projection data of the phantom comprises:

determining the actual distance D" and the actual angle $\beta_0$" by minimizing a sum of the differences of squares of the measured projection data and the calculated estimated theoretical projection data using a simplex multi-parameter optimization method.

12. A computerized tomography (CT) beam hardening correction device, comprising:

an estimated theoretical projection data calculator configured to calculate estimated theoretical projection data of each one of a plurality of phantoms based on an initial estimated position of each respective phantom relative to the ray source by using a theoretical projection data calculation model;

a phantom actual position calculator configured to calculate an actual position of each one of the plurality of phantoms relative to the ray source of the beam based on measured projection data of each phantom obtained by scanning a plurality of phantoms of different sizes by using a beam emitted by a CT device and the estimated theoretical projection data of each respective phantom;

an actual theoretical projection data calculator configured to calculate actual theoretical projection data of each one of the plurality of phantoms using the theoretical projection data calculation model according to the actual position of each respective phantom relative to the ray source of the beam;

a beam hardening correction calculation model calculator configured to obtain a beam hardening correction calculation model, wherein the beam hardening correction calculation model represents a relationship among expected projection data of a scanned object, measured projection data of the scanned object, and a beam hardening correction factor;

a beam hardening correction factor calculator configured to use the actual theoretical projection data of each one of the plurality of phantoms as the expected projection data of the scanned object, use the measured projection data of each one of the plurality of phantoms as the measured projection data of the scanned object, and calculate the beam hardening correction factor according to the relationship by using the beam hardening correction calculation model; and a measured projection data correction calculator for a measured object, configured to use measured projection data of a measured object as the measured projection data of the scanned object, and corrected projection data of the measured object as the expected projection data of the scanned object based on the calculated beam hardening correction factor, and to calculate the corrected projection data of the measured object according to the relationship.

13. A non-transitory computer-readable storage medium having instructions stored thereon that, when executed by a processor, cause the processor to perform a computerized tomography (CT) beam hardening correction method by:

scanning a plurality of phantoms of different sizes using a beam emitted via a ray source of a CT device to obtain measured projection data of the plurality of phantoms;

calculating estimated theoretical projection data of each one of the plurality of phantoms based on an initial estimated position of each respective phantom relative to the ray source using a theoretical projection data calculation model;

calculating an actual position of each one of the plurality of phantoms relative to the ray source based on the measured projection data of the phantom and the estimated theoretical projection data of each respective phantom;

calculating actual theoretical projection data of each one of the plurality of phantoms using the theoretical projection data calculation model according to the actual position of each respective phantom relative to the ray source;

obtaining a beam hardening correction calculation model, wherein the beam hardening correction calculation model represents a relationship among expected projection data of a scanned object, measured projection data of the scanned object, and a beam hardening correction factor;

using the actual theoretical projection data of each one of the plurality of phantoms as the expected projection data of the scanned object;

using the measured projection data of each one of the plurality of phantoms as the measured projection data of the scanned object;

calculating the beam hardening correction factor according to the relationship using the beam hardening correction calculation model; and using measured projection data of a measured object as the measured projection data of the scanned object and corrected projection data of the measured object as the expected projection data of the scanned object based on the calculated beam hardening correction factor; and calculating the corrected projection data of the measured object according to the relationship.

* * * * *